(12) United States Patent
Clark et al.

(10) Patent No.: US 6,642,518 B1
(45) Date of Patent: Nov. 4, 2003

(54) ASSEMBLY AND METHOD FOR IMPROVED SCANNING ELECTRON MICROSCOPE ANALYSIS OF SEMICONDUCTOR DEVICES

(75) Inventors: Fred Y. Clark, Rowlett, TX (US);
James D. Krouse, Lewisville, TX (US);
Ping Jiang, Plano, TX (US); Robyn R. Carlson, Dallas, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 10/176,873

(22) Filed: Jun. 21, 2002

(51) Int. Cl.[7] .................................. H01J 37/10
(52) U.S. Cl. ........................ 250/307; 250/311
(58) Field of Search ............................. 250/307, 492.2, 250/311

(56) References Cited

U.S. PATENT DOCUMENTS 5,798,529 A * 8/1998 Wagner .................. 250/492.2
6,410,210 B1 * 6/2002 Gabriel ........................ 430/312
2002/0134938 A1 * 9/2002 Chang et al. ................ 250/311

* cited by examiner

Primary Examiner—John R. Lee
Assistant Examiner—Phillip A Johnston
(74) Attorney, Agent, or Firm—Jacqueline J. Garner; W. James Brady, III; Frederick J. Telecky, Jr.

(57) ABSTRACT

An assembly and method for improved scanning electron microscope analysis of semiconductor devices include a structure including a first layer and a second layer, the second layer shrinking substantially when the structure is examined with a scanning electron microscope having a beam energy of at least 1.5 KeV, and at least part of the surface of the structure coated with a material composed of Iridium, wherein the coating is of sufficient thickness to reduce shrinkage of the second layer to approximately a predetermined amount when the structure is examined with a scanning electron microscope having a beam energy of at least 1.5 KeV.

21 Claims, 1 Drawing Sheet

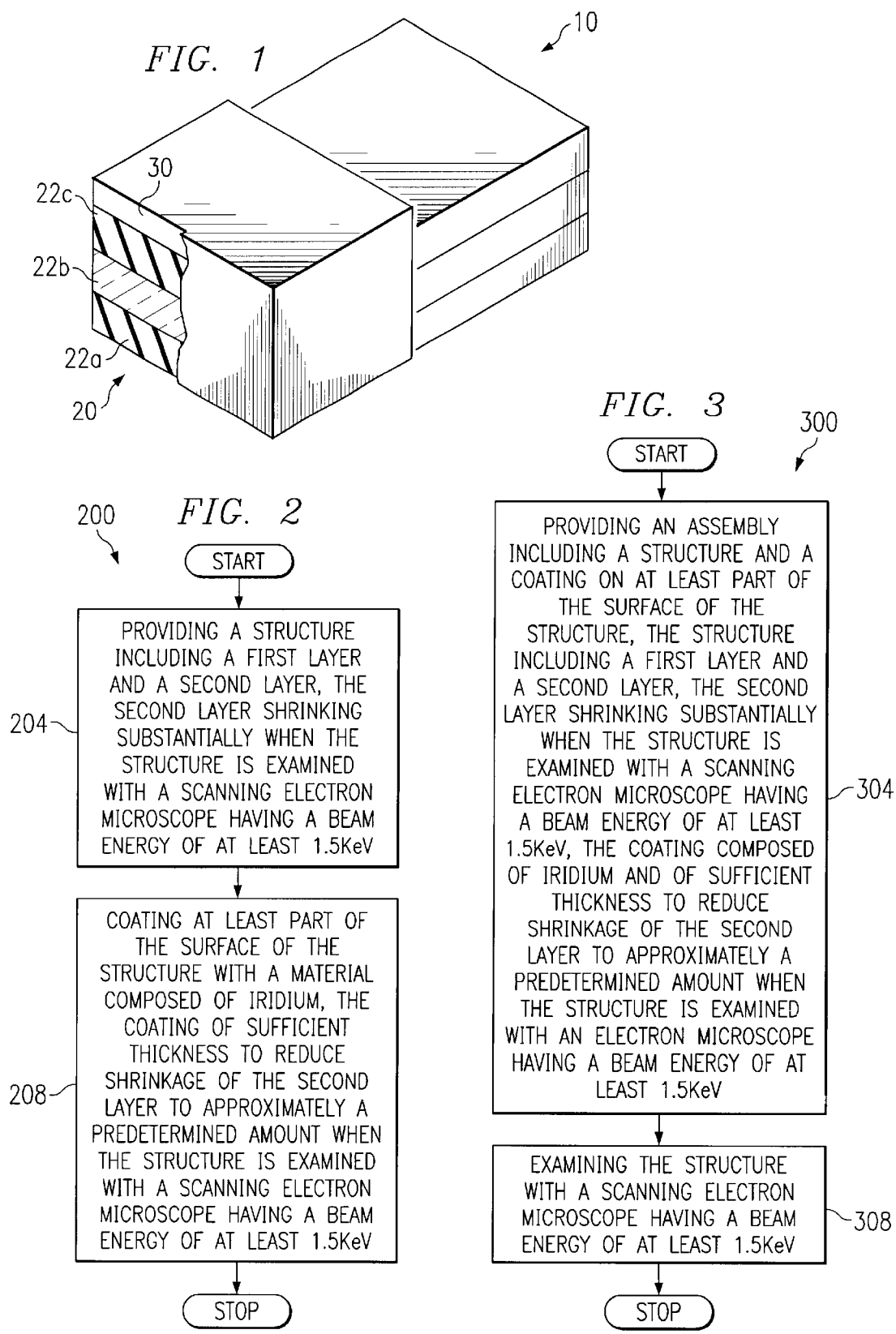

ASSEMBLY AND METHOD FOR IMPROVED SCANNING ELECTRON MICROSCOPE ANALYSIS OF SEMICONDUCTOR DEVICES

TECHNICAL FIELD OF THE INVENTION

This invention relates to semiconductor devices, and more particularly, to scanning electron microscope analysis of semiconductor devices.

BACKGROUND OF THE INVENTION

Manufacturing semiconductor devices efficiently depends on having accurate estimates of the thickness of the devices' layers, which may be as small as a few tens of nanometers currently. Underestimating the thickness of a layer may lead to improper contact, and consequently an inoperative device, due to insufficient etching. Overestimating the thickness of a layer may lead to altered electrical properties, due to excessive etching. Additionally, inaccurate estimates may cause problems with thin film deposition and cleaning. Furthermore, not being able to accurately estimate the thickness of materials used to form the devices may lead to inaccurate characterization of the etch rate itself, not to mention selectivity.

To achieve accurate estimates of the size of such small structures, manufacturers typically rely upon an electron microscope to measure the layers of sample devices. Scanning electron microscopes, for example, can typically resolve layers that are a few tens of Angstroms in thickness.

Unfortunately, scanning electron microscopes have been observed to generate inaccurate measurements for new generation semiconductor devices. Furthermore, various coatings used to reduce charge build-up on semiconductor devices being analyzed by scanning electron microscopes, such as gold, palladium, platinum, aluminum, titanium, and cobalt, may mask the structural features of the devices, making observation and analysis difficult.

SUMMARY OF THE INVENTION

The present invention substantially reduces and/or eliminates at least some of the problems and disadvantages associated with previously developed assemblies and methods for scanning electron microscope analysis of semiconductor devices. Accordingly, the present invention, at least in particular embodiments, provides a system and method for reducing deformation of a semiconductor device being examined by a scanning electron microscope while still allowing relatively small structural features of the device to be observed.

In certain embodiments, an assembly for improved scanning electron microscope analysis of semiconductor devices includes a structure and a coating on at least part of the surface of the structure. The structure includes a first layer and a second layer, the second layer shrinking substantially when the structure is examined with a scanning electron microscope having a beam energy of at least 1.5 KeV. The coating includes Iridium and is of sufficient thickness to reduce shrinkage of the second layer to approximately a predetermined amount when the structure is examined with a scanning electron microscope having a beam energy of at least 1.5 KeV.

In particular embodiments, a method for improved scanning electron microscope analysis of semiconductor devices includes providing a structure including a first layer and a second layer, the second layer shrinking substantially when the structure is examined with a scanning electron microscope having a beam energy of at least 1.5 KeV. The method also includes coating at least part of the surface of the structure with a material including Iridium, wherein the coating is of sufficient thickness to reduce shrinkage of the second layer to approximately a predetermined amount when the structure is examined with a scanning electron microscope having a beam energy of at least 1.5 KeV.

The present invention possesses several technical features. For example, because the coating may prevent at least one layer of the structure from shrinking substantially when the structure is being examined by a scanning electron microscope, measurements of the layers of the structure may be made with increased accuracy. This allows increased semiconductor manufacturing efficiency, due to reduction of etching, thin film deposition, and cleaning problems because of inaccurate estimates and to better characterization of the etch rate itself and selectivity. Moreover, because materials that shrink substantially during scanning electron microscope analysis often have low dielectric constants, which reduces the overall capacitance of a transistor and, consequently, increases switching speed, improving the efficiency with which transistors including these materials may be manufactured may lead to faster, cheaper computers. As an additional example, the coating allows relatively small features of the structure to be observed, which assists in analyzing a semiconductor device.

Particular embodiments, of course, may possess one, some, or all of these technical features and/or additional technical features. Other technical features will be readily apparent to those skilled in the art from the following figures, detailed description, and/or claims.

BRIEF DESCRIPTION OF THE DRAWINGS

The drawings described below provide a more complete understanding of the present invention, especially when considered in conjunction with the following detailed description, and also of its technical features:

FIG. 1 illustrates an assembly for improved scanning electron microscope analysis of semiconductor devices in accordance with one embodiment of the present invention;

FIG. 2 is a flowchart illustrating a method for improved scanning electron microscope analysis of semiconductor devices in accordance with one embodiment of the present invention; and FIG. 3 is a flowchart illustrating a method for improved scanning electron microscope analysis of semiconductor devices in accordance with another embodiment of the present invention.

DETAILED DESCRIPTION OF THE INVENTION

FIG. 1 illustrates an assembly 10 for improved scanning electron microscope analysis of semiconductor devices in accordance with one embodiment of the present invention. As illustrated, assembly 10 includes a structure 20 and a coating 30. In general, structure 20 is part of a semiconductor device to be analyzed with a scanning electron microscope, and coating 30 reduces deformation of the structure due to the examination.

In more detail, structure 20 includes layers 22a–c. Layer 22a and layer 22c may be composed of any appropriate material, may have any appropriate shape, and may have any appropriate dimension for forming part of a semiconductor device. In particular embodiments, layer 22a and layer 22c are part of a transistor. For example, layer 22a may be a substrate, such as, for example, a wafer, and may be composed of any appropriate type of semiconductive material, such as, for example, single crystalline silicon. As another example, layer 22a may be a layer of semiconductive material formed on a substrate, such as, for example, an epitaxial layer grown on a wafer. As a further example, layer 22a may be a gate electrode and may be composed of any appropriate conducting material, such as, for example, polycrystalline silicon. As an additional example, layer 22c may be a spacer to prevent material that reacts with layer 22a, such as, for example, dopant or silicide, from coming too close to layer 22a and may be composed of any appropriate material, such as, for example, nitride. As a further example, layer 22a and layer 22c may be layers used in "back-end" processing of semiconductor devices. In certain embodiments layer 22a and layer 22c are composed of Silicon Carbide (SiC) and have a thickness of approximately 1,000 Angstroms and 400 Angstroms, respectively. Layer 22a and layer 22c may be formed by any of a variety of techniques well known to those skilled in the art.

Layer 22b may also have any appropriate shape and any appropriate dimension for forming part of a semiconductor device. In particular embodiments, layer 22b may be part of a transistor. For example, layer 22b may be a gate dielectric, which serves to insulate the rest of a gate structure from a semiconductive layer. As another example, layer 22b may insulate a gate electrode from electrical current during the operation of the transistor. As an additional example, layer 22b may be used in "back-end" processing of semiconductor devices. In a particular embodiment, layer 22b is approximately 5,700 Angstroms thick.

Layer 22b may be composed of any appropriate type of material that shrinks substantially when structure 20 is examined with a scanning electron microscope. In general, shrinkage is substantial when it materially affects the measurements of structure 20. For example, shrinkages of greater than ten percent are unacceptable for numerous manufacturing applications.

In particular embodiments, layer 22b is composed, at least in part, of a material having at least a "low" dielectric constant, typically less than about 4.2. In certain embodiments, layer 22b may be composed of organosilicate glass (OSG), which has a dielectric constant between approximately 2.7–3.0. In some embodiments, layer 22b may be composed of hydrogen silsequioxane (HSQ) or methyl silsequioxane (MSQ), which have "ultra-low" dielectric constants. In other embodiments, layer 22b may be composed, at least in part, of a material that has a high porosity. Layer 22b may be formed on layer 22a or on layer 22c by any of a variety of techniques well known to those skilled in the art.

Note that shrinkage of layer 22b may depend on the surrounding layers. For example, when layer 22b is composed of OSG, the shrinkage is magnified when layer 22a is composed of SiC, composed of a thin layer $Si_3N_4$, or is absent. As another example, if layer 22a is composed of copper or if there are other layers on top of layer 22a, the shrinkage may be reduced.

Coating 30 covers at least part of the surface of structure 20 and, as mentioned previously, acts to reduce deformation of structure 20 when it is being examined with a scanning electron microscope. In general, coating 30 is composed of Iridium. In particular embodiments, coating 30 consists essentially of Iridium.

Coating 30 may be applied to structure 20 by any appropriate technique. In particular embodiments, coating 30 is applied by a sputter deposition process. For instance, coating 30 may be applied by placing structure 20 in an Emitech K575X with a target composed of Iridium.

In embodiments where layer 22b is composed of OSG and layer 22a and layer 22c are composed of SiC, depositing Iridium for between approximately forty and seventy seconds with a K575X results in a coating approximately ten Angstroms thick. Such a coating may reduce shrinkage of layer 22b, which creates problems in measuring layers 22 of structure 20, to less than two percent, and probably to less than two-tenths of one percent, when examined with a scanning electron microscope having a beam energy of approximately 1.5 KeV. Additionally, the coating may still allow relatively small features, possibly down to a few tens of Angstroms, of structure 20 to be observed. Coating 30 may also prevent layer 22b from shrinking substantially at even higher beam energies, such as, for example, 5.0 KeV. The thickness of coating 30 may need to be adjusted for other low dielectric materials.

Assembly 10 possesses several technical features. For example, because coating 30 may prevent layer 22b from shrinking substantially when structure 20 is being examined by a scanning electron microscope, measurements of structure 20 may be made with increased accuracy. This allows increased semiconductor manufacturing efficiency, due to the reduction of etching, thin film deposition, and cleaning problems because of inaccurate estimates and to better characterization of the etch rate itself and selectivity. Moreover, because materials that shrink substantially during scanning electron microscope analysis often have low dielectric constants, which results in the reduction of the overall capacitance of a transistor and, consequently, increases switching speed, improving the efficiency with which transistors including those materials may be manufactured may lead to faster, cheaper computers. As an additional example, because coating 30 allows relatively small features of structure 20, possibly layers 22 themselves, to be observed, analysis of structure 20 is improved. As still a further example, coating 30 may reduce charging of structure 20. A variety of other technical features exist.

Although FIG. 1 illustrates one embodiment of an assembly for improved scanning electron microscope analysis of semiconductor devices in accordance with the present invention, other embodiments may have less, more, and/or a different arrangement of components. For example, in certain embodiments, one or both of layer 22a and layer 22c may not be used. As another example, in some embodiments, additional layers may be used. As a further example, in particular embodiments, layer 22b may be underneath layer 22a or on top of layer 22c. A variety of other examples exist.

FIG. 2 is a flowchart 200 illustrating a method for improved scanning electron microscope analysis of semiconductor devices in accordance with one embodiment of the present invention. The method begins at function block 204 with providing a structure including a first layer and a second layer, the second layer shrinking substantially when the structure is examined with a scanning electron microscope having a beam energy of at least 1.5 KeV. As mentioned previously, the structure could be part of a transistor or any other semiconductor device, and the second layer could be composed of a material having at least a low dielectric constant. At function block 208, the method continues with coating at least part of the surface of the structure with a material composed of Iridium, the coating of sufficient thickness to reduce shrinkage of the second layer to approximately a predetermined amount when the structure is examined with a scanning electron microscope having a beam energy of at least 1.5 KeV. As mentioned previously, the coating could be approximately ten Angstroms thick and could reduce shrinkage to two percent or less. Additionally, the coating could be formed by any appropriate technique well known to those skilled in the art.

Although flowchart 200 illustrates one method for improved scanning electron microscope analysis of semiconductor devices in accordance with the present invention, other embodiments may have less, more, and/or a different arrangement of operations. For example, in certain embodiments, the structure may have additional layers. As another example, the coating could be thick enough to reduce shrinkage of the structure to approximately two percent or less in some embodiments. A variety of other examples exist.

FIG. 3 is a flowchart 300 illustrating a method for improved scanning electron microscope analysis of semiconductor devices in accordance with another embodiment of the present invention. The method begins at function block 304 with providing an assembly including a structure and a coating on at least part of the surface of the structure, the structure including a first layer and a second layer, the second layer shrinking substantially when the structure is examined with a scanning electron microscope having a beam energy of at least 1.5 KeV, the coating composed of Iridium and of sufficient thickness to reduce shrinkage of the second layer to approximately a predetermined amount when the structure is examined with a scanning electron microscope having a beam energy of at least 1.5 KeV. As mentioned previously, the structure could be part of a transistor or any other semiconductor device, and the second layer could be composed of a material having at least a low dielectric constant. Also as mentioned previously, the coating could be approximately ten Angstroms thick and could reduce shrinkage to two percent or less. At function block 308, the method calls for examining the structure with a scanning electron microscope having a beam energy of at least 1.5 KeV.

Although flowchart 300 illustrates one method for improved scanning electron microscope analysis of semiconductor devices in accordance with the present invention, other embodiments may have less, more, and/or a different arrangement of operations. For example, in certain embodiments, the structure may have additional layers. As another example, the coating could be thick enough to reduce shrinkage of the second layer to two percent or less in some embodiments. As an additional example, in certain embodiments, the coating could also prevent the structure from shrinking more than two percent. A variety of other examples exist.

While a variety of embodiments have been discussed for the present invention, a variety of additions, deletions, modifications, and/or substitutions will be readily suggested to those skilled in the art. It is intended, therefore, that the following claims encompass such additions, deletions, modifications, and/or substitutions.

What is claimed is:

1. An assembly for improved scanning electron microscope analysis of semiconductor devices, comprising:
   a structure comprising a first layer and a second layer, the second layer shrinking substantially when the structure is examined with a scanning electron microscope having a beam energy of at least 1.5 KeV; and
   a coating on at least part of the surface of the structure, the coating comprised of Iridium and of sufficient thickness to reduce shrinkage of the second layer to approximately a predetermined amount when the structure is examined with a scanning electron microscope having a beam energy of at least 1.5 KeV.

2. The assembly of claim 1, wherein the structure comprises a transistor.

3. The assembly of claim 1, wherein the second layer comprises a material having at least a low dielectric constant.

4. The assembly of claim 3, wherein the material comprises organo-silicate glass.

5. The assembly of claim 1, wherein the predetermined amount is two percent.

6. The assembly of claim 1, wherein the coating is approximately ten Angstroms thick.

7. A method for improved scanning electron microscope analysis of semiconductor devices, comprising:
   providing a structure comprising a first layer and a second layer, the second layer shrinking substantially when the structure is examined with a scanning electron microscope having a beam energy of at least 1.5 KeV; and
   coating at least part of the surface of the structure with a material comprising Iridium;
   wherein the coating is of sufficient thickness to reduce shrinkage of the second layer to approximately a predetermined amount when the structure is examined with a scanning electron microscope having a beam energy of at least 1.5 KeV.

8. The method of claim 7, wherein the structure comprises a transistor.

9. The method of claim 7, wherein the second layer comprises a material having at least a low dielectric constant.

10. The method of claim 9, wherein the material comprises organo-silicate glass.

11. The method of claim 7, wherein coating at least part of the surface of the structure comprises sputter depositing the material on the structure.

12. The method of claim 7, wherein the predetermined amount is two percent.

13. The method of claim 7, wherein the coating is approximately ten Angstroms thick.

14. A method for improved scanning electron microscope analysis of semiconductor devices, comprising:
- providing an assembly, comprising:
    - a structure comprising a first layer and a second layer, the second layer shrinking substantially when the structure is examined with a scanning electron microscope having a beam energy of at least 1.5 KeV, and
    - a coating on at least part of the surface of the structure, the coating comprised of Iridium and of sufficient thickness to reduce shrinkage of the second layer to approximately a predetermined amount when the structure is examined with a scanning electron microscope having a beam energy of at least 1.5 KeV; and
- examining the structure with a scanning electron microscope having a beam energy of at least 1.5 KeV.

15. The method of claim 14, wherein the structure comprises a transistor.

16. The method of claim 14, wherein the second layer comprises a material having at least a low dielectric constant.

17. The method of claim 16, wherein the material comprises organo-silicate glass.

18. The method of claim 14, wherein the predetermined amount is two percent.

19. The method of claim 14, wherein the coating is approximately ten Angstroms thick.

20. The method of claim 14, wherein the scanning electron microscope has a beam energy of at least 5.0 KeV.

21. An assembly for improved scanning electron microscope analysis of semiconductor devices, comprising:
- a structure comprising a first layer and a second layer, the second layer comprising a material having at least a low dielectric constant; and
- a coating of Iridium on at least part of the surface of the structure, the coating of sufficient thickness to reduce shrinkage of the second layer to approximately one-tenth of one percent when the structure is examined with a scanning electron microscope with a beam energy of at least 1.5 KeV.

* * * * *